(12) United States Patent
Hastings et al.

(10) Patent No.: US 6,341,233 B1
(45) Date of Patent: Jan. 22, 2002

(54) DEVICE FOR MAINTAINING A NATURAL HEART RHYTHM

(75) Inventors: David Hastings, Lake Oswego, OR (US); Max Schaldach, Erlangen (DE); Gary Rolison, Portland; Robert R. Weyant, Dureham, both of OR (US)

(73) Assignee: Biotronik Mess-Und Therapiegerate GmbH & Co., Berlin (DE)

( * ) Notice: Subject to any disclaimer, the term of this patent is extended or adjusted under 35 U.S.C. 154(b) by 0 days.

(21) Appl. No.: 09/281,875

(22) Filed: Mar. 31, 1999

(30) Foreign Application Priority Data

Mar. 31, 1998 (DE) .......................................... 198 15 539

(51) Int. Cl.[7] .............................................. A61N 1/362
(52) U.S. Cl. ...................................................... 607/9
(58) Field of Search ............................. 607/9, 123, 25; 600/509, 515, 516

(56) References Cited

U.S. PATENT DOCUMENTS

| | | |
|---|---|---|
| 4,917,115 A | 4/1990 | Flammang et al. |
| 5,584,867 A | 12/1996 | Limousin et al. |
| 5,628,777 A | 5/1997 | Moberg et al. |
| 5,720,768 A * | 2/1998 | Verboven-Nelissen ......... 607/9 |
| 5,913,887 A * | 6/1999 | Michel ....................... 607/123 |

FOREIGN PATENT DOCUMENTS

WO    WO 97/22380    6/1997

\* cited by examiner

Primary Examiner—Jeffrey R. Jastrzab
(74) Attorney, Agent, or Firm—Merchant & Gould P.C.

(57) ABSTRACT

Device for maintaining or restoring a natural heart rhythm through the generation of an electrical stimulation signal, in particular in the form of an implantable heart pacemaker, which device shows two sensors arranged inside the body of the patient for picking up a body-specific signal that contains information concerning the demand for heart performance or another magnitude relevant to the heart. Connected to the downstream side of the sensors is a processing unit that obtains, from the temporal difference of a body-specific signal received one after another at both sensors, a body-specific time-delay signal, which represents the length of the determined time delay. The body-specific time-delay signal forms at least indirectly a control signal that influences the point in time and/or the time sequence of the stimulation signal.

8 Claims, 1 Drawing Sheet

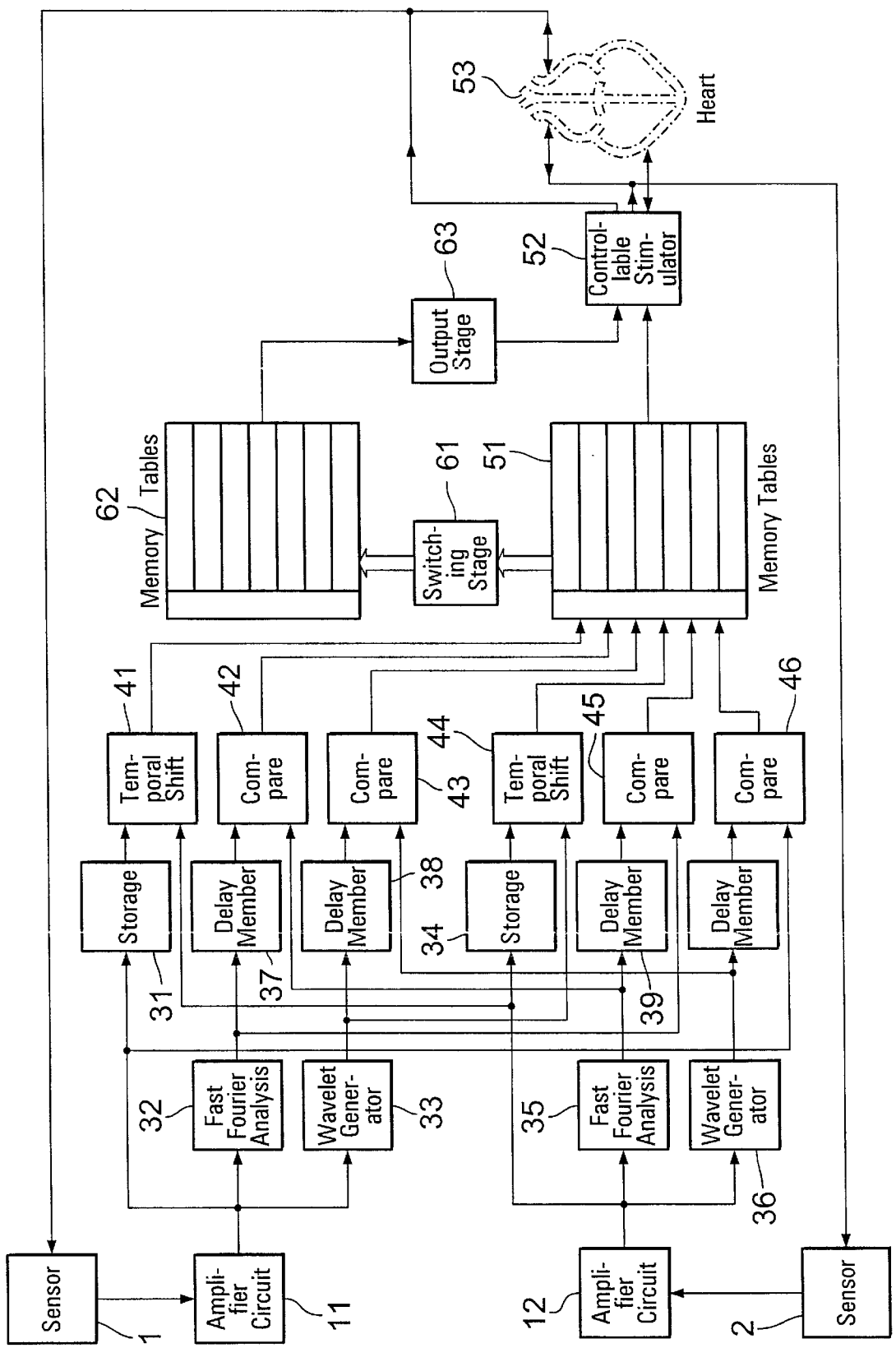

US 6,341,233 B1

DEVICE FOR MAINTAINING A NATURAL HEART RHYTHM

TECHNICAL FIELD

The invention concerns a device according to the pre-characterizing clause of Claim 1.

BACKGROUND

Known from the prior art are manifold devices that display at least one sensor arranged inside the body of the patient for receiving a body-specific measurement signal containing information concerning demand for heart performance, in order to derive therefrom, among other things, a signal for influencing the stimulation rate.

Devices in existence until now started out from the fact that there exists a direct and time-correct relationship between the change in the body-specific measurement signal containing information concerning demand for heart performance and the stimulation magnitude to be influenced, as for example the amplitude, the rate or the average frequency or occurrence of signals picked up by a sensor, and the heart rate.

However, it has been shown that a direct processing of this type in the time or frequency domain often does not lead to the desired results.

Therefore, the task underlying the invention is to improve the controlling of stimulation events and, more particularly, of the heart rate.

SUMMARY

The task, starting out from a device based on the precharacterizing clause in Claim 1, is accomplished by the features given in the characterizing part of Claim 1.

The invention includes the technical teaching that in the determination of a magnitude influencing the stimulation signal sequence, those relationships also should be observed that extend beyond a direct association. Relating to this, on the one hand, is a transformation of the time periods to be considered in such a manner that periodic observation also takes place over past time periods, and that control of the heart rate is checked by the spatial-temporal displacement of complex frequency sequences or event sequences that show time delays within the body. These time delays are obtained through the temporal displacement of two measurement-values that are picked up in a spatially displaced manner. The agreement of the underlying event signals is preferably verified here by pattern comparison. The time delays of the frequency or event sequences are determined here by the circulatory dynamic and the body-internal regulating processes underlying this.

In this manner, it is possible to "decode" a body-specific dynamic and to make it accessible for heart stimulation, which dynamic, to be sure, until now has already played an important role in controlling the vasomotor system of the human body, but could not be used for reconstructing natural heart rhythm.

In the case of the signals to be evaluated, we are dealing with circulation magnitudes whose constant fluctuation in dynamic variations also contains information concerning demand for heart performance. Here, we are dealing specifically with time delays of electrical signals in the heart. In particular, characteristic here is the A—A conduction, which, when it exceeds or falls below characteristic values, is an early sign of a threatening tachycardia or fibrillation. That the time-delay difference between the two atriums is too large must be recognized early enough to prevent through biatrial stimulation the initiation of a tachycardia. Thus, by evaluation of the corresponding signal time-delay, countermeasures that prevent a corresponding state, for example biatrial stimulation sequences, can be taken early enough.

Associated with the invention is the important advantage that, for the first time, signals that until now were not capable of being detected, or that remained unobserved, co-determine the stimulation rate, so that sensors detecting the physical activity of the patient can be dispensed with.

The use of the device in accordance with the invention for maintaining or restoring a natural heart rhythm by generating an electrical stimulation signal relates, in particular, to implantable heart pacemakers for treating bradycardia or tachycardia, as well as corresponding hearty-rhythm correcting devices, which are also in use as implantable defibrillators.

If, according to the invention, there is connected to the downstream side of a sensor a processing unit that obtains from the measurement signal a body-specific time-delay signal whose duration covers a range from a few milliseconds up to a second, whereby the body-specific time-delay signal forms at least indirectly a control signal that influences the point in time, or the time sequence and/or the point in time, of the stimulation signal, then this means that information is taken from a time-delay signal impressed on the circulation system or the nervous system that is of significance for heart activity. It has been found that these signals are also of significance for human heart activity, and a stimulation in correlation to such signals forms at least a physiological supplement to signals that are relevant for heart function and picked up some other way from the patient's body.

The selection of the body-specific time-delay signal can be accomplished by means of digital filtering or use of a correlation technique.

In the case of a digital processing, there also exists the possibility of effecting, in advantageous fashion, a detection or a synchronization of the time-delay processes by comparison of complete signal patterns within the amplitude and/or frequency range. Here, in particular in the processing unit, selected by means of a time window within a time segment of a predetermined duration comprising less than 100 milliseconds, is at least one periodically-occurring signal, or a corresponding portion of a signal, having a characteristic amplitude response or frequency pattern, and derived from the sequence of the appearance of this pattern is the body-specific time-delay signal that influences the time sequences or the point in time of the stimulation signal. The width of the time segments to be used in this processing corresponds here to the time delays of the expected signals or signal portions. A determination of a control signal based on the similarity or matching of amplitude or frequency patterns appearing in the time delay includes the advantage that a similarity of the signal portions determining the time-delay frequency is recognized more rapidly and more reliably even in the case of less-frequently repeating periods, and the "build up" of filter circuits or the like need not be waited upon in order to detect the periodic signal portions. This is particularly convenient in the case of longer delay times.

Here, for detection of coincident signal patterns, is stored in particular the periodically appearing signal or a corresponding signal portion picked up in each case in the time segment, having a characteristic amplitude response or frequency pattern, whereby the pattern of the current time segment is compared with at least one similar periodically-occurring signal picked up earlier or with a corresponding signal portion having a characteristic amplitude response or frequency pattern and, in coincidence with the later-appearing, periodically-occurring signal or corresponding signal portion having a characteristic amplitude response or frequency pattern, a control signal is emitted when the degree of conformity of the patterns to be compared with one another exceeds a predetermined value, whereby derived from the signal indicating the conformity is the control magnitude that influences the magnitude of the stimulation. In place of the frequency pattern, it is also possible here to compare the time response of one or several spectral portions in the frequency pattern that was (were) picked up within a time segment (wavelet).

The control magnitude, which influences the time sequence or the point in time of the stimulation signal, can here also be derived from the rate, the average frequency, the temporal change of the rate or of the average frequency, of the signal indicating conformity, so that there results a statistical compression of the derived information that is drawn upon for the stimulation. A corresponding compression of the information can also be achieved if the information from the amplitude response pattern and from the spectral pattern is evaluated together.

For generating frequency spectra, the time-dependent signal is appropriately subjected to a Fast-Fourier-Transformation (FFT).

Coming into consideration as body-specific sensor signals that are subjected to the processing in accordance with the invention are, in particular, characteristic portions of the intracardial electrogram, the A—A interval, the interarterial stimulus speed, and other heart-internal time delays.

Other advantageous developments of the invention are characterized in the dependent claims or are represented in more detail in the following with the aid of the figures, together with the description of the preferred implementation of the invention.

DESCRIPTION

The single FIGURE shows a preferred from of implementation of the invention as a block diagram.

In the implementation example represented in the figure, we are dealing with a device for maintaining or restoring a natural heart rhythm by generating an electrical stimulation signal, the device being in the form of an implantable pacemaker that displays at least one sensor arranged inside the patient's body for picking up a body-specific signal containing information concerning demand for heart performance, or some other heart-relevant magnitude. One such magnitude is represented likewise by the heart-internal time-delay signal between the two atriums.

In this, connected downstream of the sensors 1 and 2 is a processing unit consisting of several elements to be described in the following, which processing unit obtains from the measurement signals supplied to these sensors (represented by input arrows) a body-specific time-delay signal whose duration comprises at least a few milliseconds. The body-specific time-delay signal forms at least indirectly a control signal that influences the point in time, or the time sequence or the point in time, of the stimulation signal.

In the case of sensors 1 and 2, it can be a matter here of electrodes attached in the region of the two atrium of the heart.

However, also coming into consideration as input signals are the intracardial electrogram, the intracardial or transthoracic impedance, blood temperature, vagal/parasympathetic or baroreceptive nerve signals, intra-arterial pressure or the pressure difference picked up at two different measurement locations, the electrochemical cellular ionic potential, or others.

For this, the selection of the body-specific time-delay signal takes place in the components in the top part of the figure, within a frequency range that essentially corresponds to the day/night rhythm, and thus to the inner human clock. On the other hand, there takes place in the lower part of the figure a selection of the body-specific time-delay signal within a frequency region which essentially corresponds to a 6- to 20-second rhythm, in particular a 10-second rhythm. It thus corresponds to a fraction of the breathing rate. In the drawing, provided in blocks 11 and 12 are amplifier circuits for the signals picked up by the sensors. Stored in blocks 31 and 34 in storage components is the amplitude response determined in each case over a time segment of the sensor signal. In blocks 41 and 44 there takes place, for the respective signals within a time window adapted to the time delay of the signal, a determination of the temporal shift of the later signal relative to the earlier picked-up A-event of the other chamber in each case.

In the representation in the figure, the time delay of the two A—A events relative to each other is determined in two processing branches (upper and lower part). Thus, in the course of a cycle there result two time delays, each of the A-events in the two chambers being regarded once as the preceding one.

The ascertaining of the agreement of the signal with that which was expected takes place through pattern or similarity comparison. When the agreement has been ascertained, the time interval is determined and this is further processed as the signal that is characteristic of the dynamic.

A Fast Fourier Analysis is performed in stages 32 and 35, so that serving as a signal pattern for the comparison, in stages 42 and 45 respectively, of the signal currently appearing with a signal that is time-delayed in a delay member 37 or 39 respectively, is the average frequency spectrum in the respective time segment.

In stages 33 and 36, instead of this, wavelets are generated and —after a delay in delay members 38, 40—are likewise compared with one another in stages 43 and 46, so that from the repetition of corresponding wavelets a conclusion can be reached concerning the periodicity of the corresponding sensor signal.

Here, selected and retained in the processing unit within a time segment of predetermined duration, comprising at least several seconds, is at least one periodically appearing signal or a corresponding signal portion having a characteristic amplitude response or frequency pattern.

The periodically-occurring signal picked up in each case in the time segment, or a corresponding signal portion having a characteristic amplitude response or frequency pattern, is stored in the subsequent stages, the current time segment is compared with at least one similar, previously-picked-up, periodically-occurring signal or a corresponding signal portion having a characteristic amplitude response or frequency pattern, and a control signal is emitted in coincidence with the later-appearing, periodically-occurring signal or a corresponding signal portion having a characteristic amplitude response, when the degree of conformity of the patterns to be compared with one another exceeds a predetermined value. The periodicity of the dynamic signals thus results from the signal delaying of successive signals, which is necessary for causing these signals (whether they are the amplitude response or the spectrum) to coincide with their predecessors according to a matching or correlation process.

The output signals from stages 41 to 46 therefore represent the periodicity, determined in each case by the kind of processing means 31 to 46, of the time delays of the dynamic signal portions detected in the input signals by sensors 1 and 2. By addressing a subsequent memory formed as a reference table, the combination of the output signals of stages 41 to 46 occurs, which are representative of the periodicity of the signals, as addressing signals for the memory, which, in turn, sends the control sequences stored at the addressed locations in the memory to the conventional heart pacemaker or defibrillator. Here, it is a matter of a rate control signal of a unique signal for triggering an individual tachycardia-terminating or defibrillation sequence.

It can be seen that through the combination of the output signals of stages 41 to 46 complex evaluations of the body-specific time-delay signals can be undertaken. For this, coming into consideration in particular are their logical operations, overlays, time derivations, accumulation values, etc.

The contents of the addressed memory locations of the tables memory 51 emit an output signal to the otherwise-conventional, controllable stimulator part 52, which, in known manner, is in interaction with the heart 53. In the case of a rate-controlled pacemaker, the basic rate is influenced by the control signals from the output of memory 51, while in the case of a defibrillator a defibrillation cycle is executed whenever the body time-delay signals exceed a predetermined threshold value. Since with this device we are dealing with one in which a body-specific time-delay magnitude that influences the stimulation of the heart can itself be influenced by body-internal coupling, there can exist—as with any control system—the danger of a tendency to oscillation. Therefore, to avoid this, means are planned that, in the case of an excessive increase of the average amplitude of a magnitude characteristic of the circulatory dynamic, implement appropriate countermeasures. Used by stages 41 to 46 in addressing the tables memory 51 for this purpose is not only the time interval of the consecutive pattern signals that is characteristic of the internal circulatory dynamic in each case, but also the average amplitude of the pattern signals. If this amplitude exceeds a predetermined maximum value, then addressed via a switching stage 61 is another tables memory 62, which effects, via an output stage 63, a change of the stimulation magnitude in proportion to the course of the temporal change of the ascertained body time-delay magnitude, by a predetermined or a statistically-determined delay value.

The invention is not limited in it implementation to the preferred implementation example given above. To the contrary, a number of variants are possible that make use of the represented solution in implementations of fundamentally different types.

What is claimed is:

1. A device for maintaining or re-establishing a natural heart rhythm by generating an electrical stimulation signal, the device having the form of an implantable heart pacemaker, comprising:

two sensors adapted to be arranged inside a patient's body for picking up one or more body-specific signals containing information relevant to the patient's heart, the two sensors being adapted for generating a signal that is proportional to a body-specific time delay signal; and a processing unit connected downstream of the two sensors for obtaining, from the temporal difference of the one or more body-specific signals received at the two sensors, the proportional body-specific time-delay signal that represents the duration of the ascertained time delay wherein the proportional body-specific time-delay signal forms at least a control signal for influencing the point in time or the time sequence of the stimulation signal and the selection of the proportional body-specific time-delay signal occurs by means of digital filtering or by the use of a correlation technique.

2. A device for maintaining or re-establishing a natural heart rhythm by generating an electrical stimulation signal, the device having the form of an implantable heart pacemaker, comprising:

two sensors adapted to be arranged inside a patient's body for picking up one or more body-specific signals containing information relevant to the patient's heart, the two sensors being adapted for generating a signal that is proportional to a body-specific time delay signal; and a processing unit connected downstream of the two sensors for obtaining, from the temporal difference of the one or more body-specific signals received at the two sensors, the proportional body-specific time-delay signal that represents the duration of the ascertained time delay and determines a therapy dependent upon the proportional body-specific time-delay signal.

wherein the proportional body-specific time-delay signal forms at least a control signal for influencing the point in time or the time sequence of the stimulation signal, and wherein selected in the processing unit within a time segment of a predetermined duration and comprising less than 100 milliseconds is a characteristic signal selected from the group consisting of at least one periodically-appearing signal, a corresponding signal portion having a characteristic amplitude response and a frequency pattern, and wherein the proportional body-specific time-delay signal is derived from the succession of the appearance of the frequency pattern, and wherein the proportional body specific time-delay signal influences the time sequence or the point in time of the stimulation signal, and wherein, the sequential time segments displays a predetermined interval that corresponds to the expected length of the time delay; and wherein the characteristic signal picked up in each case in the time segment and appearing in a time-displaced manner, having a characteristic amplitude response or frequency pattern, is stored, and wherein the current time segment is compared with at least one similar characteristic signal appearing in a time-displaced manner, having a characteristic amplitude response or frequency pattern, and wherein in coincidence with the later appearing signal, a time signal is emitted that indicates the time difference of appearance when the degree of conformity of the patterns to be compared with one another exceeds a predetermined value, and wherein the proportional body-specific time-delay signal is generated from the timing signal.

3. A device for maintaining or re-establishing a natural heart rhythm by generating an electrical stimulation signal, the device having the form of an implantable heart pacemaker, comprising:

two sensors adapted to be arranged inside a patient's body for picking up one or more body-specific signals containing information relevant to the patient's heart, the two sensors being adapted for generating a signal that is proportional to a body-specific time delay signal; and a processing unit connected downstream of the two sensors for obtaining, from the temporal difference of the one or more body-specific signals received at the two sensors, the proportional body-specific time-delay signal that represents the duration of the ascertained time delay wherein the proportional body-specific time-delay signal forms at least a control signal for influencing the point in time or the time sequence of the stimulation and the temporal courses of one or more spectral portions in the frequency pattern are compared.

4. A device for maintaining or re-establishing a natural heart rhythm by generating an electrical stimulation signal, the device having the form of an implantable heart pacemaker, comprising:

two sensors adapted to be arranged inside a patient's body for picking up one or more body-specific signals containing information relevant to the patient's heart, the two sensors being adapted for generating a signal that is proportional to a body-specific time delay signal; and a processing unit connected downstream of the two sensors for obtaining, from the temporal difference of the one or more body-specific signals received at the two sensors, the proportional body-specific time-delay signal that represents the duration of the ascertained time delay wherein the proportional body-specific time-delay signal forms at least a control signal for influencing the point in time or the time sequence of the stimulation signal and the proportional body-specific time-delay signal is generated from the superposition or accumulation of several proportional body-specific time-delay signals selected from the group consisting of the rate, the average frequency, the temporal change of the rate and the temporal average frequency, of a signal indicating conformity, for at least two time segments of different duration.

5. A device for maintaining or re-establishing a natural heart rhythm by generating an electrical stimulation signal, the device having the form of an implantable heart pacemaker, comprising:

two sensors adapted to be arranged inside a patient's body for picking up one or more body-specific signals containing information relevant to the patient's heart, the two sensors being adapted for generating a signal that is proportional to a body-specific time delay signal; and a processing unit connected downstream of the two sensors for obtaining from the temporal difference of the one or more body-specific signals received at the two sensors, the proportional body-specific time-delay signal that represents the duration of the ascertained time delay and determines a therapy dependent upon the proportional body-specific time-delay signal, wherein the proportional body-specific time-delay signal forms at least a control signal for influencing the point in time or the time sequence of the stimulation signal, and wherein selected in the processing unit within a time segment of a predetermined duration and comprising less than 100 milliseconds is a characteristic signal selected from the group consisting of at least one periodically-appearing signal, a corresponding signal portion having a characteristic amplitude response and a frequency pattern, and wherein the proportional body-specific time-delay signal is derived from the succession of the appearance of the frequency pattern, and wherein the proportional body specific time-delay signal influences the time sequence or the point in time of the stimulation signal, and wherein, the sequential time segments displays a predetermined interval that corresponds to the expected length of the time delay; and wherein the control magnitude that influences the time sequence or the point in time of the stimulation signal is generated by the superposition or accumulation of several proportional body specific time-delay signals selected from the group consisting of the rate, the average frequency, the temporal change of the rate and wherein the temporal average frequency, of a signal indicating conformity, for at least two time segments of the same duration which is evaluated, on the one hand, the amplitude response and, on the other hand, the course of the frequency pattern.

6. A device for maintaining or re-establishing a natural heart rhythm by generating an electrical stimulation signal, the device having the form of an implantable heart pacemaker, comprising:

two sensors adapted to be arranged inside a patient's body for picking up one or more body-specific signals containing information relevant to the patient's heart, the two sensors being adapted for generating a signal that is proportional to a body-specific time delay signal; and a processing unit connected downstream of the two sensors for obtaining, from the temporal difference of the one or more body-specific signals received at the two sensors, the proportional body-specific time-delay signal that represents the duration of the ascertained time delay and determines a therapy dependent upon the proportional body-specific time-delay signal, wherein the proportional body-specific time-delay signal forms at least a control signal for influencing the point in time or the time sequence of the stimulation signal, and wherein selected in the processing unit within a time segment of a predetermined duration and comprising less than 100 milliseconds as a characteristic signal selected from the group consisting of at least one periodically-appearing signal, a corresponding signal portion having a characteristic amplitude response and a frequency pattern, and wherein the proportional body-specific time-delay signal is derived from the succession of the appearance of the frequency pattern, and wherein the proportional body specific time-delay signal influences the time sequence or the point in time of the stimulation signal, and wherein, the sequential time segments displays a predetermined interval that corresponds to the expected length of the time delay; and wherein the frequency patterns is subjected to a Fast-Fourier-Transformation.

7. A device for maintaining or re-establishing a natural heart rhythm by generating an electrical stimulation signal, the device having the form of an implantable heart pacemaker, comprising:

two sensors to be arranged inside a patient's body for picking up one or more body-specific signals containing information relevant to the patient's heart, the two sensors being adapted for generating a signal that is proportional to a body-specific time delay signal; and a processing unit connected downstream of the two sensors for obtaining, from the temporal difference of the one or more body-specific signals received at the two sensors, the proportional body-specific time-delay signal that represents the duration of the ascertained time delay wherein the proportional body-specific time-delay signal forms at least a control signal for influencing the point in time or the time sequence of the stimulation signal and upon determination of an excessive rise in amplitude of the current temporal value of the proportional body-specific time-delay signal, in comparison to an earlier-occurring long term average value of the proportional body-specific time-delay signal, the phase position of the change of the stimulation magnitude is changed in proportion to the course of the temporal change of the determined time-delay magnitude, by a predetermined or statistically-determined magnitude.

8. A device for maintaining or re-establishing a natural heart rhythm by generating an electrical stimulation signal, the device having the form of an implantable heart pacemaker, comprising:

two sensors adapted to be arranged inside a patient's body for picking up one or more body-specific signals containing information relevant to the patient's heart, the two sensors being adapted for generating a signal that is proportional to a body-specific time delay signal; and a processing unit connected downstream of the two sensors for obtaining, from the temporal difference of the one or more body-specific signals received at the two sensors, the proportional body-specific time-delay signal that represents the duration of the ascertained time delay wherein the proportional body-specific time-delay signal forms at least a control signal for influencing the point in time or the time sequence of the stimulation signal and comparisons of signals selected from the group consisting of patterns, spectra and signal courses are carried out by least square error metered.

* * * * *